US011636945B1

(12) United States Patent
Gallegos et al.

(10) Patent No.: US 11,636,945 B1
(45) Date of Patent: Apr. 25, 2023

(54) PRACTITIONER REFERRAL PLATFORM

(71) Applicants: Hugo Gallegos, Fairview, OR (US); Gail Tasch, Eau Claire, WI (US)

(72) Inventors: Hugo Gallegos, Fairview, OR (US); Gail Tasch, Eau Claire, WI (US)

(73) Assignee: Mediverity, Inc., Eau Claire, WI (US)

( * ) Notice: Subject to any disclaimer, the term of this patent is extended or adjusted under 35 U.S.C. 154(b) by 660 days.

(21) Appl. No.: 16/598,200

(22) Filed: Oct. 10, 2019

Related U.S. Application Data

(60) Provisional application No. 62/743,804, filed on Oct. 10, 2018.

(51) Int. Cl.
| | | |
|---|---|---|
| *G16H 40/20* | (2018.01) | |
| *G06Q 10/06* | (2012.01) | |
| *G06F 16/9035* | (2019.01) | |
| *G06F 16/248* | (2019.01) | |
| *G06F 16/2457* | (2019.01) | |
| *G06Q 10/0639* | (2023.01) | |

(52) U.S. Cl.
CPC .......... *G16H 40/20* (2018.01); *G06F 16/248* (2019.01); *G06F 16/24578* (2019.01); *G06F 16/9035* (2019.01); *G06Q 10/06398* (2013.01)

(58) Field of Classification Search
CPC . G16H 40/20; G06F 16/24578; G06F 16/248; G06F 16/9035; G06Q 10/06398
USPC ........................................................ 705/2–3
See application file for complete search history.

(56) References Cited

U.S. PATENT DOCUMENTS

| 8,694,441 | B1 | 4/2014 | Rothschild et al. | |
| 2010/0228564 | A1* | 9/2010 | Kharraz Tavakol | .... G16Z 99/00 |
| | | | | 705/317 |
| 2010/0235295 | A1* | 9/2010 | Zides | ................. G06Q 30/0282 |
| | | | | 705/347 |
| 2015/0278222 | A1* | 10/2015 | Claussenelias | ... G06F 16/24578 |
| | | | | 707/723 |
| 2016/0140301 | A1* | 5/2016 | Richter | .................. G16H 70/00 |
| | | | | 705/2 |
| 2017/0053543 | A1* | 2/2017 | Agrawal | ................ A61B 90/37 |

OTHER PUBLICATIONS

Driscoll et al., Video Assessment of Basic Surgical Trainees' Operative Skills, The American Journal of Surgery, 2008, vol. 196, pp. 265-272, doi: 10.1016/j.amjsurg.2007.09.044 (Year: 2008).*

* cited by examiner

*Primary Examiner* — Joy Chng
(74) *Attorney, Agent, or Firm* — Anthony J. Bourget

(57) ABSTRACT

A searchable practitioner referral platform, system and method utilizing multiple self-reported objective factors of a practitioner which carry weighted scores based on a frequency of the factor, the weighted scores having a maximum count frequency and accumulating to a total score recalculated for reporting, and where the system is a practitioner-only system utilized in one aspect by a practitioner only after the practitioner inputs his or her own data factor information.

22 Claims, 14 Drawing Sheets

PRACTITIONER REFERRAL PLATFORM

CROSS-REFERENCE TO RELATED APPLICATIONS

This application claims the benefit and priority of Provisional Patent Application Ser. No. 62/743,804, filed Oct. 10, 2018 for Practitioner Referral Platform, incorporated herein by reference in its entirety for continuity of disclosure.

BACKGROUND OF THE INVENTION

1. Field of the Invention

This invention relates to platforms, systems and methods of providing practitioner information based on multiple data factors, including providing information regarding healthcare practitioners.

2. Background Information

There are systems for ascertaining the quality of a professional or for searching and ranking healthcare providers based on their background and experience. Examples of some of these include systems or methods shown in U.S. Pat. No. 8,694,441 and U.S. Patent App. No. US 2015/0278222. While these and other systems and method have benefits, there is room for improvement.

SUMMARY OF THE INVENTION

In one aspect the invention is a practitioner-only referral platform providing ranked scores of practitioners based on self-reported objective factors. Practitioners such as physicians (or other professional groups) may filter the pool of peers based on specialty interest and area of expertise (or other criteria) to find potential practitioners for referral purposes. In various aspects the invention includes a platform or web portal where a practitioner undertakes searches for referral of his or her patients to various practitioners based on ranked scoring. In further aspects the invention includes a computer implemented system and methods utilized by a practitioner to make referrals. In still further aspects the invention includes use of pricing data or scoring and rankings alone or in combination with quality comparisons or quality scoring and quality rankings. In still further aspects the invention includes use of data concerning peer review of practitioner skill videos.

In a further aspect the invention includes a system and computer-implemented method of utilizing multiple self-reported factors which carry weighted scores based on the frequency of the occurrence of the factor. In one example a doctor receives additional scoring or points for each hospital affiliation (up to a set maximum), and the weighted points and maximum frequency of counting the points is determined based on preference or expertise of the system creator or administrator. Once the scores are totaled from the various factors they are recalculated based on a range of 1-100 (or other selected range). Physicians or administrators of a hospital or clinic or service organization, for instance, may self-report the data/factors for each practitioner. In addition to practitioner referring usage, data/scoring is available for hospitals/clinics. The scoring and ranking is based on actual objective data. In further aspects pricing information is also displayed and ranked in combination with quality data of practitioners. In further aspects some factors include peer review of practitioner skills videos.

In some examples the self-reported data includes numerous objective factors which are weighted according to preselected preferences based on the experience of the owner/operator of the scoring system. Determining a relative weighting of the factors and which of many factors to utilize is based on preference and experience of the system owner/operator and algorithms that may vary based on time and experience. Practitioners may input data in various stages through a series of input screens or surveys and/or download/upload forms to be populated with the requested information and included in a database of information pertaining to the practitioners.

In a further aspect of the invention a practitioner will be unable to review the peer scores and ranking unless he or she enters his or her own data for scoring (or consents or directs a third party to enter his or her data). The system and methods are limited to practitioners by requiring, for instance, input of an NPI number, license number, board certification field or other verifying information. In further aspects, subsystems are utilized to confirm/check or match the self-reported information to validate or authenticate that the physician is in fact a physician and authorized to access the system and methods.

In a further aspect the invention includes a peer assessment (subjective input) whereby a video of a surgeon or other practitioner performing an activity is uploaded by the practitioner for review by peers. A peer assessment of a surgeon's actions (operative skill, communication manners or other aspects) is based on feedback and scoring for creation of a peer score. Mechanisms are provided to assure only true peers are able to review like-peers. Once the peer score is established it is factored into a report score of the practitioner for access by any practitioner in the system (or limited as desired by the operator of the system).

The above partial summary of the present invention is not intended to describe each illustrated embodiment, aspect, or every implementation of the present invention. The figures and detailed description and claims that follow more particularly exemplify these and other embodiments and further aspects of the invention.

Figure 1:
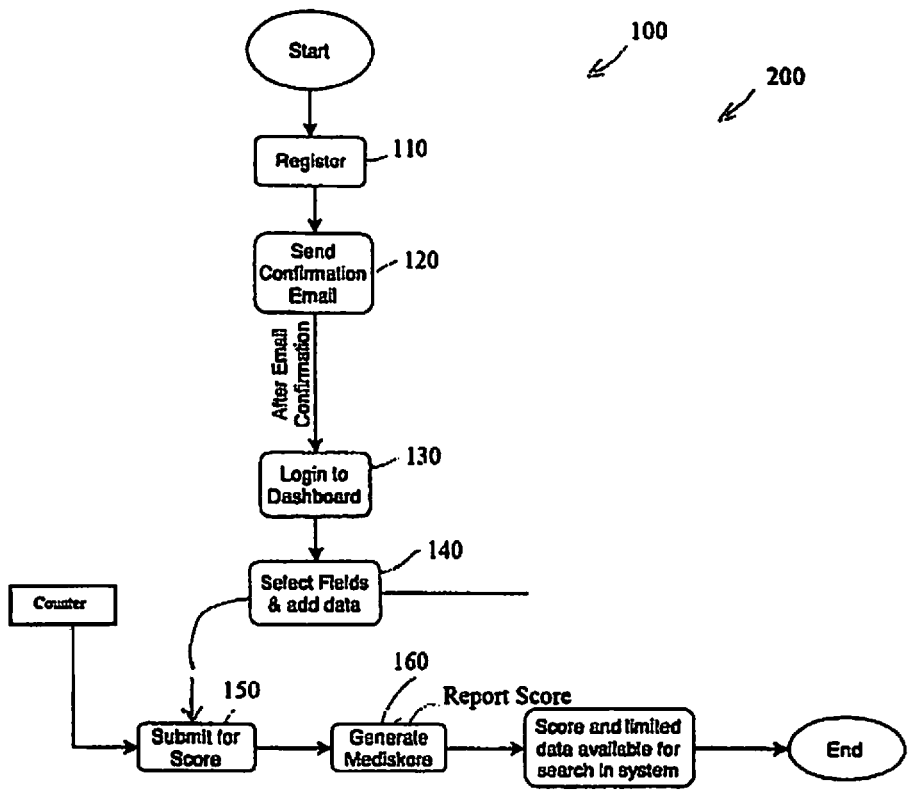
FIG. 1 is a flow diagram illustrating a system and process in accordance with an embodiment of the present invention.

While the invention is amenable to various modifications and alternative forms, specifics thereof have been shown by way of example in the drawings and will be described in detail. It should be understood, however, that the intention is not necessarily to limit the invention to the particular embodiments, aspects and features described. On the contrary, the intention is to cover all modifications, equivalents, and alternatives falling within the spirit and scope of the invention and as defined by the appended claims.

DETAILED DESCRIPTION OF THE INVENTION

Referring to FIGS. 1-15, systems and methods in accordance with aspects of the invention are shown. In FIG. 1, a computer implemented method 100 includes registration of a user 110. In one aspect of the invention, registration 110 of a user includes registration of practitioner-only users. For instance, in one aspect only physicians or other medical practitioners (medical doctors, physician assistants, dentists, nurse practitioners, chiropractors, optometrists, podiatrists, registered nurses, psychologists, naturopathic practitioners, certified registered nurses, audiologists, physical therapists, etc.) are permitted to use the method 100 and systems. A physician, for instance, will provide his or her name, profession, specialty, License number, Board Certification, NPI, Provider Taxonomy Code, and Geo-location upon registration. The NPI number is a National Provider Identifier, a unique 10-digit number provided to healthcare providers or practitioners. The NPI number is included in The NPI Registry Public Search, which is a free directory of all active NPI records, with portions published, such as the provider's name, specialty (taxonomy) and practice address, and is downloadable and/or supplied via an Application Programming Interface (API). This data is collected to assure that only permitted practitioners are allowed to participate in the system. In other aspects the system is adapted to be used for other professional referrals (accountants, attorneys, engineers, teachers/coaches, business executives, plumbers, or other groups maintaining certifications or standards).

Figure 4:
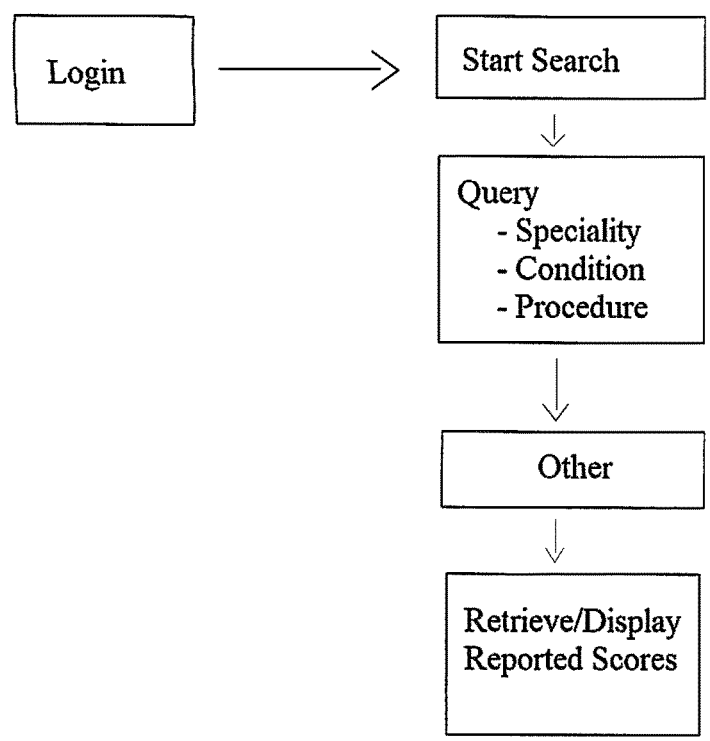
FIG. 4 is a flow diagram illustrating a system and process in accordance with an aspect of the present invention.

Once a practitioner is registered, a confirmation email or other message is sent 120 and dashboard login 130 is enabled. A practitioner may use password and user name or other login methods to login 130 to a dashboard via a website configured to receive queries and display results. Query fields are provided to filter the pool of practitioners so a search can be narrowed to a desired specialty, health condition, medical procedure, location, or other criteria. For instance, a general practice physician seeking to refer a patient to a dermatologist or cataract surgeon will input the filtered information to retrieve a set of candidate practitioners. FIG. 4 shows a typical flow of login, query input and retrieval or display of reported practitioners and ranked scoring.

The dashboard login 130 may include both the query fields (or links to the fields) for a practitioner to conduct referral searching and/or a portal and mechanisms for entering his or her practitioner information. A Select Fields and Add Data module 140 allows the practitioner (or an assistant of the practitioner, for instance) to select fields and upload or otherwise register data pertaining to a variety of objective factors. Many, most or all of the fields contain preselect data in drop-down menus for easy input of data. Details of the flow within module 140 are explained further below. Once all of the fields and data have been registered or entered at module 140 (or even If partially registered or entered), a raw score is received or submitted at module or step 150. The raw score is adjusted to derive or generate a Mediskore™ or report score 50, 160 for the practitioner. In one instance the report score is a numerical score based on a 0-100 range or 0-200 range (other identifiers or ranges or scales may be used). The Report Score 160 and other data are stored in a database available for search within the system and method 100.

Figure 2:
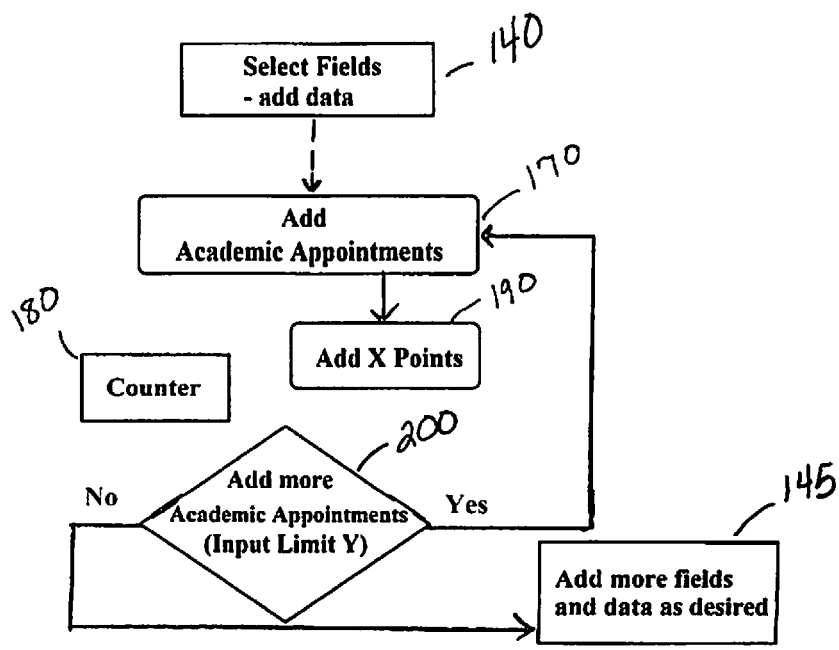
FIG. 2 is a flow diagram illustrating an aspect of the system and process of FIG. 1.

System and method 100 utilized module 140 for the selection and compiling of objective data to be used in scoring and generating a Report Score 160. Module 140 is configured to receive information pertaining to numerous fields or data factors. In one aspect, each data factor is an objective factor. In a non-limiting representative example, a set of data factors may include the following: education, years of experience, training, hospital appointments, academic appointments, hospital affiliations, disciplinary/legal, licensure, board certifications, areas of expertise, membership affiliations, insurance accepted, clinical trials, patents, presentations, publications, research, awards, professional development education, athletic teams, social media, media and press, community involvement, volunteer programs, type of practice, foreign language. Each data factor is or may receive an associated score as established herein, such as an education score, years of experience score, training score, hospital appointments score, academic appointments score, hospital affiliations score, disciplinary/legal score, licensure score, board certifications score, areas of expertise score, membership affiliations score, insurance accepted score, clinical trials score, patents score, presentations score, publications score, research score, awards score, professional development education score, athletic teams score, social media score, media and press score, community involvement score, volunteer programs score, type of practice score, foreign language score. In further examples, the data factors 170 may include data and associated scores pertaining to:

Education
Fellowship Training
Residency Training
Internship Training
Hospital Appointments
Academic Appointments
Hospital Affiliations
Disciplinary Actions
Disciplinary Actions Administrative Action
Malpractice Judgments
Criminal Offense
Active Physician Licensure Status
Board Certification(s)
Special Interest Area of Expertise
NPI
Controlled Substance Prescriber
Provider Taxonomy Code
DEA License
Membership Affiliation(s)
Insurance Accepted
Clinical Trials
Patents
Presentations
Publications
Book Chapter(s)
Articles
Research
Awards
Professional Development Education
Athletic Team(s)
Social Media Network(s)
Media & Press
Community Involvement
Volunteer Charity Program(s)
Type of Practice
Foreign Language
Operative Skill With reference to FIG. 2, the Select Fields and Add Data step and module 140 is configured to undertake several collecting or recording steps for each data factor 170. FIG.

2 shows the addition of the Academic Appointments data factor 170. For instance, if a practitioner has an Academic Appointment, such information is noted (by checking a box and/or uploading the relevant information regarding the Academic Appointment) and a numerical value "X" is added to a running count maintained at a counter 180 for instance. The numerical value "X" is a number established by the owner/operator/programmer ("Administrator") of system 100. In this case the Administrator is applicant. This value "X" is based on the Administrator's subjective opinion concerning the relative weighting of importance of the data factor 170. This subjective opinion and value "X" is based on the Administrator's experience. The value "X" may vary over time based on different criteria, including the subjective opinion regarding change of relevance of the particular data factor 170 in relation to other data factors 170. The value "X" may also be tied to different factors 170 and an automatic balance or adjustment to the value "X" in one aspect is made depending on other criteria (such as X is initially set to a value of "1" (or other number), and automatically changes to a value of "2" (or other value) as some other factor 170 is reported.

In one aspect, the value of "X" is set and not altered (or rarely altered). In one aspect, such as regarding Add Academic Appointments 170, the value of "X" is set at 3 points. The value of "3" is added to the counter 180 at step 190. If there is an additional Academic Appointment to report or record ("Yes" at step 200), the practitioner will enter the additional Academic Appointment at 170 (by increasing the value at an input field or scroll bar, for instance) which will add "X" points 190 to counter 180. In this example, where the value "X" is set at "3 points", the counter will have increased a total of 6 points (due to the objective fact that the practitioner has 2 Academic Appointments). The process loop at 200 repeats until there are no more Academic Appointments 170 to report (i.e., "No" at step 200) or a total of "Y" occurrences have been met. For instance, Administrator sets "Y" to a limit of 5 Academic Appointments, so that the total score or addition to the counter 180 can be no greater than "15" (3 points×5 occurrences=15). Administrator may set the value of "Y" as desired, based on the same or similar criteria for setting the value of "X" noted above. Administrator has great flexibility in establishing the upper limit of the total scoring value for a particular data factor 170 by establishing a large value "X" to be multiplied by a large value "Y". The X and Y values may be any number, including negative numbers in the case of data factors 170 that reflect poorly on a practitioner (i.e., disciplinary actions or other factors 170). For instance, a value of "X" may be negative 1 for a disciplinary action or a negative "3" for a disciplinary administrative action. In such case the value in the counter 180 is reduced in number. In a further aspect with respect to FIG. 2, Administrator sets the valued "X" for Academic Appointments at "4" and allows a limit value "Y" of "10" for the loop or repeat step 200 for a maximum added score/counter value of "40." Other values may be used as desired. If there are no more Academic Appointments 170, the condition 200 is "NO" and the flow proceeds to adding the next data factor 170 at step 145. The counter 180 is adjusted (or might not change) at each additional data factor 170.

Figure 3:
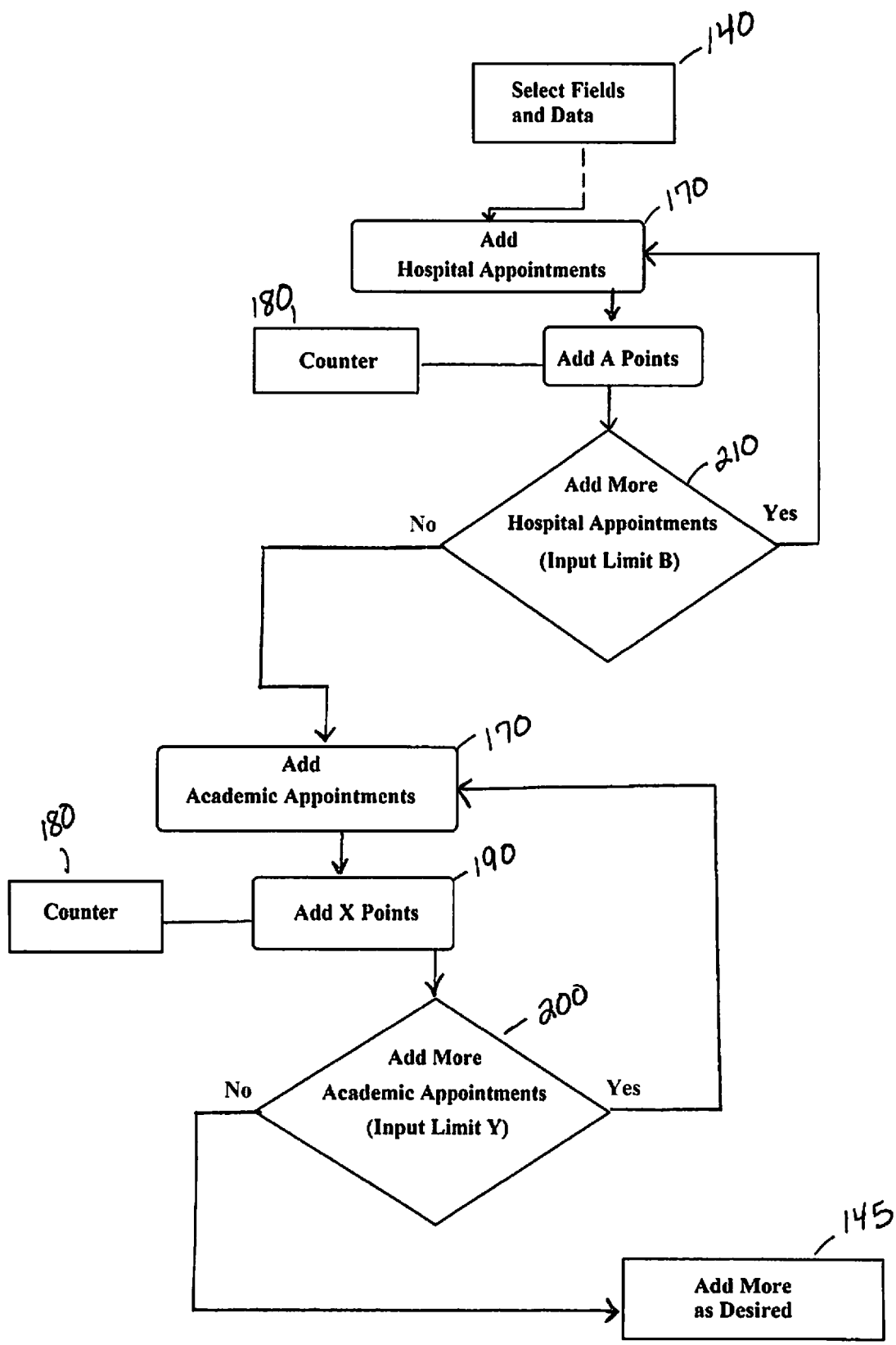
FIG. 3 is a flow diagram illustrating further aspects of the system and process of FIG. 1.

FIG. 3 is a flow diagram presenting a further feature of Select Fields and Add Data 140. In this diagram, Administrator has configured system and method 100 to allow input of a data factor 170 for Hospital Appointments. If the practitioner has a Hospital Appointment, that fact is noted (by checking a box or advancement of a roller number or selection of a data element in a drop down menu or other counting mechanism) in which case the value "A" is added to counter 180. In other aspect the name of a hospital or school or other data is selected from a pull down menu and added to the practitioner's profile, and the number of data items entered is multiplied by the weighted amount (up to a certain number of data items that are input and/or set by the programmer/Administrator. Administrator sets the value "A" using criteria the same or similar to that described above for setting the values of "X" and "Y". For instance, "A" may be set at 2 points so that for each Hospital Appointment the counter 180 is increased by 2. The Administrator, based on his or her experience, trial and error, research or other criteria, will establish "2" as a designated weighted value. If there are additional Hospital Appointments, the flow is configured to allow for adding more of this data factor ("Yes" at condition 210) so that additional "A" values are added to the count. In some instances a user may select a button called "Add More" to add additional data factor 170 information. A limit of "B" is set by the Administrator at condition 210 in order to limit the number of loops or occurrences of Hospital Appointments that may be recognized for increasing the scoring. In one non-limiting example, "B" is set at "10" and "A" set at "2" such that the maximum addition of scoring to counter 180 is 20 (2×10=20). If for instance, a practitioner has 3 Hospital Appointments 170, upon entry of this information the total score increases by a value of "6" (2×3=6). If there are no more Hospital Appointments 170, the condition 200 is "NO" and the flow proceeds to adding the next data factor 170 at step 145, or as noted below.

In further reference to FIG. 3, the Add Hospital Appointments data factor 170 is immediately followed by the Add Academic Appointments 170 referenced above. In alternatives, different data factors 170 are included and may precede or follow any other data factor(s) as desired by Administrator. In some aspect not all of the data factors 170 noted above will be configured into system or method 100, or all of those factors noted above are configured into the system, or additional data factors 170 may be included. The system and software may be configured to account for addition of the various data factors in a "series" relationship, where the count is incremented sequentially; in other aspects the system or portions of the systems may be arranged in parallel where multiple data factors 170 and associated values for counter 180 are added simultaneously or in different orders. The sequence of adding data factors 170 may be interrupted, paused and later continued as needed or desired. The system is configured to achieve an accurate and objective total score for reporting, and thus the manner and sequence of the collection in some aspects is secondary to assuring accurate scoring. A data file may be formatted, then populated by a practitioner, and then uploaded into the system 100 to arrive at a total score or counter value. In some instances, the values or scores may tally into the hundreds or even thousands of points/value. The counter value or total score in one aspect is reworked to be expressed on a different scale, such as a scale of 0-100. After undertaking input or recording of all or several data factors 170 (and there may be several as listed above), a very large numerical total score may be achieved for a particular practitioner. For instance, a practitioner may receive a total score of over several hundred, such as 850, and other practitioners may receive total scores of 1,222, or 475, or whatever depending on the objective data factors 170 pertaining to the particular practitioner. In one aspect these scores are converted to a score on the 0-100 range or 0-200 range (or other range) as a Report Score.

Figure 5:
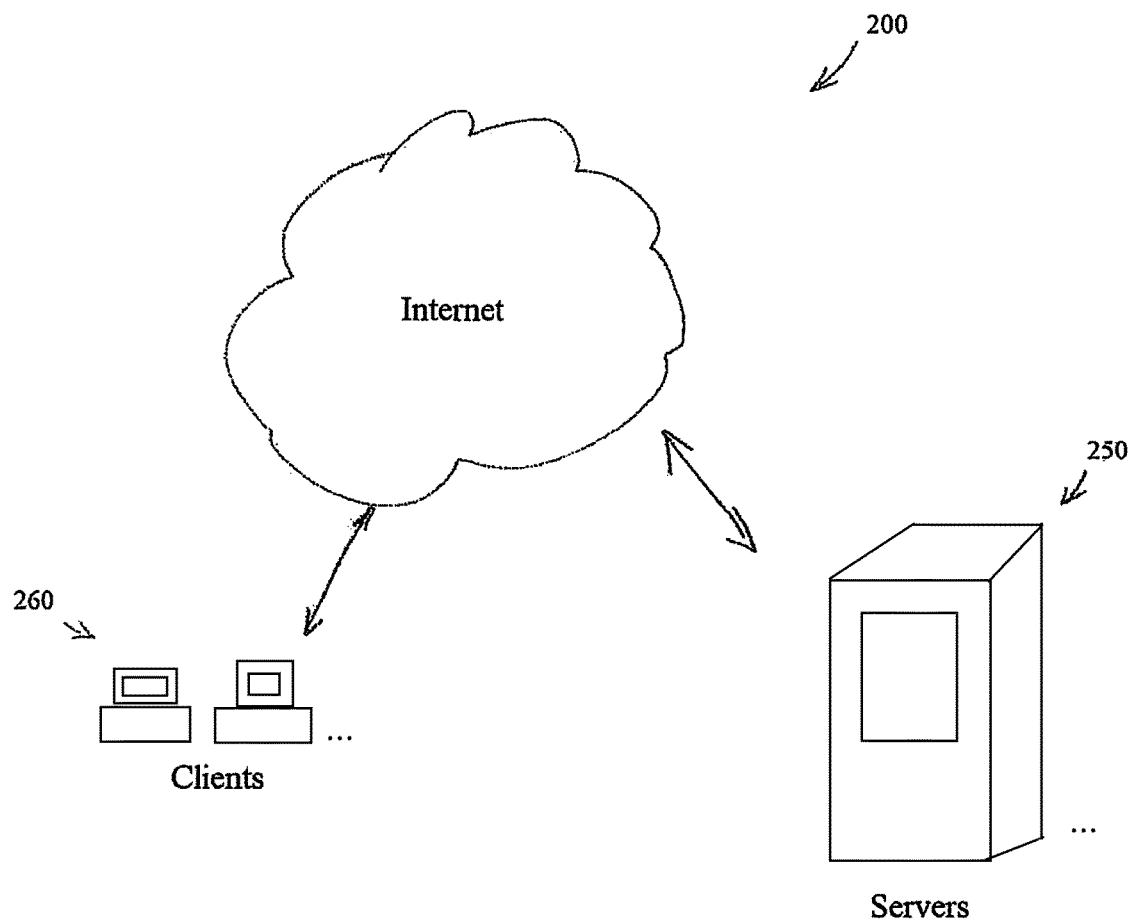
FIG. 5 is a schematic diagram of a system in accordance with an aspect of the present invention.
Figure 6:
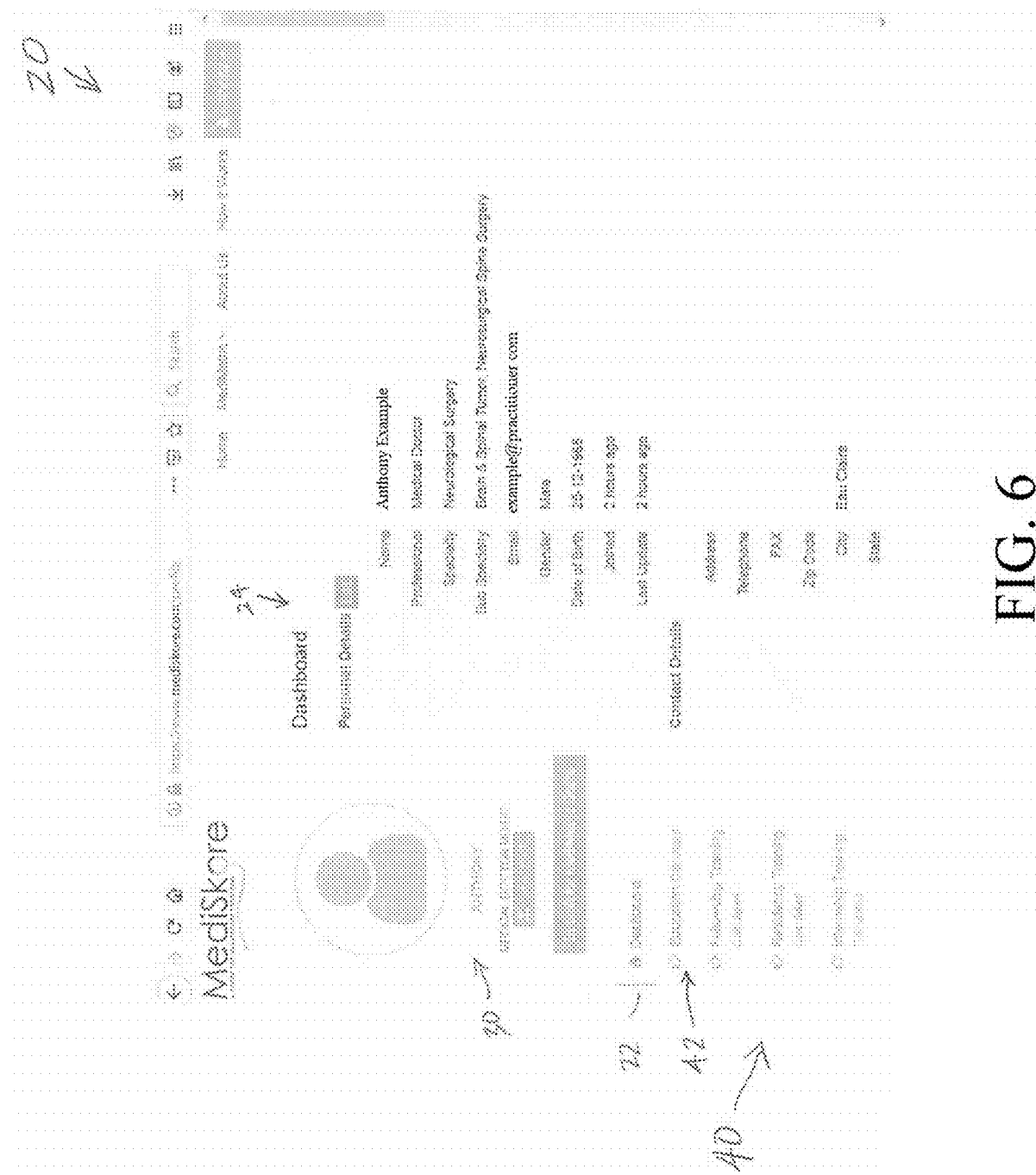
FIG. 6 is a screen shot in accordance with one aspect of the present invention.
Figure 7:
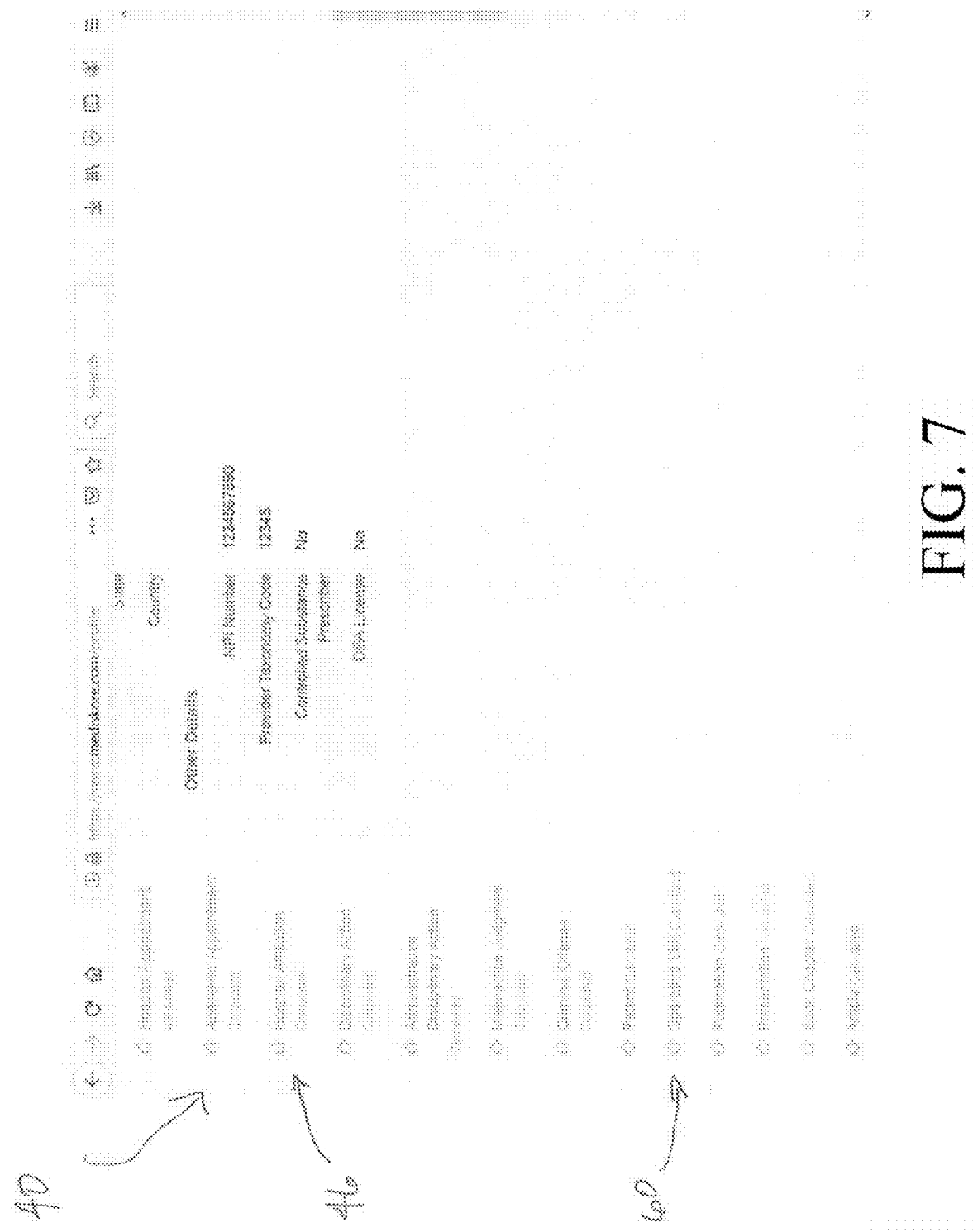
FIG. 7 is a screen shot in accordance with one aspect of the present invention.
Figure 8:
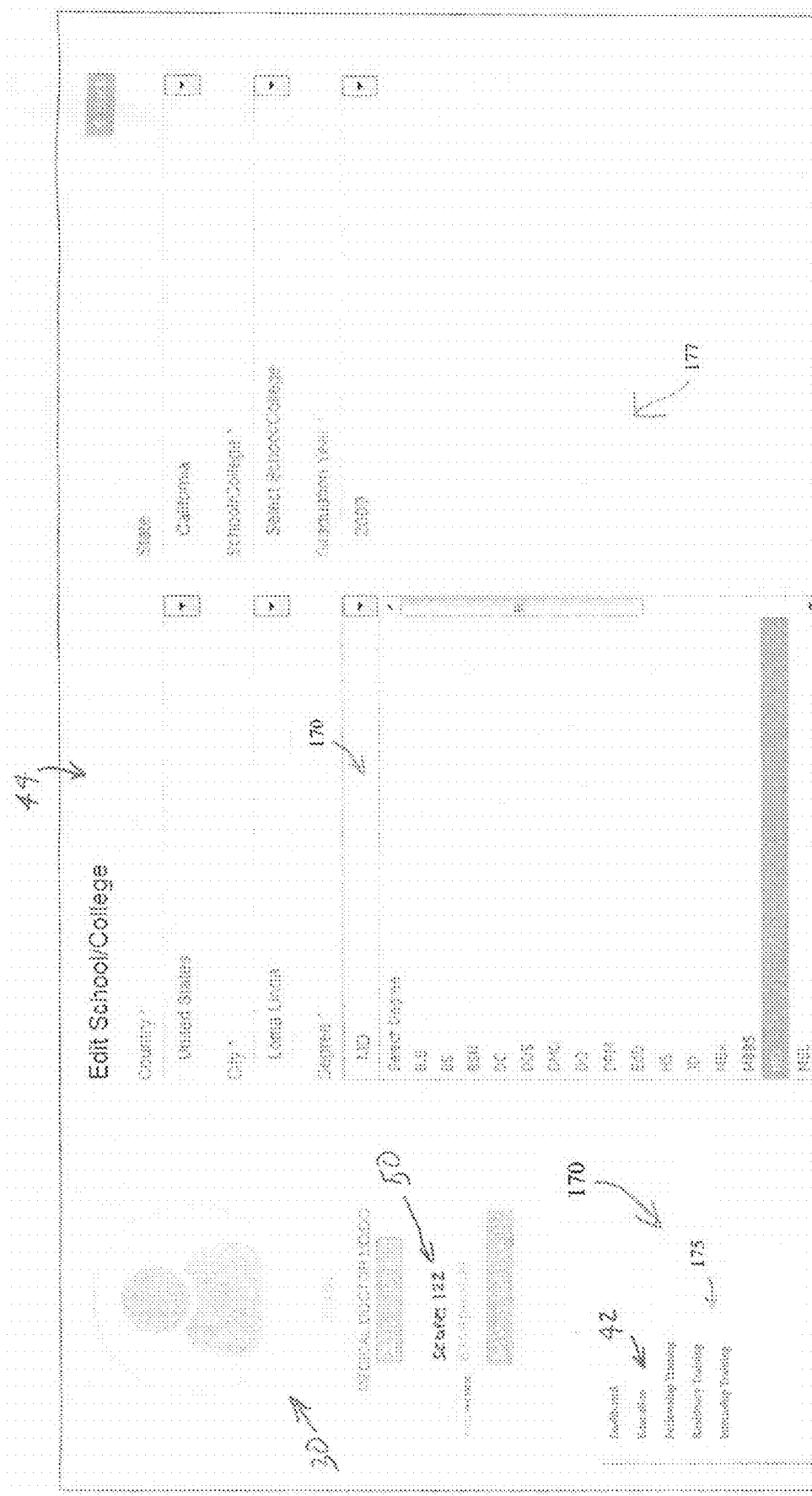
FIG. 8 is a screen shot in accordance with an aspect of the present invention.
Figure 9:
FIG. 9 is a screen shot in accordance with an aspect of the present invention.

FIG. 5 is a diagram of a system 200 which implements method 100. A server 250 or several servers 250 are configured with processors and memory and associated databases with connection to each other via a LAN and/or to the cloud or Internet whereby a client computer 260 or several client computers 260 or computing devices (laptop computers, tablet computers, mobile devices) 260 may access data and undertake searches by utilizing the software and information provided by servers 250. A registered practitioner may login to the system 200 at a client computer 260, for instance, and run search queries to find referrals. The search queries return ranked list of practitioners based on the Report Score for each practitioner.

FIG. 6 through FIG. 9 are representative screen shots of a web page in accordance with a system and method aspect of the invention. The web page layout may be modified to fit a particular case as desired. In one aspect, a webpage 20 is displayable on a user interface and includes a Dashboard tab 22 which opens a dashboard field 24 for entry or upload of profile information of a practitioner 30. Information such as name, address, email address, password, license numbers, NPI number, specialty, sub-specialty and other data is obtained at Dashboard and may be edited as needed. An NPI Number (See FIG. 7) must be included in order to become a registered practitioner-user 32. In one aspect a column of data factor tabs 140 is provided for selection and entry of various data factors 170. In one aspect, an education tab 42 opens an education field 44 (FIG. 8) having pull down menus and pre-populated lists for easy entry or selection of schools and curricula. Multiple schools may be easily inserted. Counter 180 is activated and/or points are added to a raw score to calculate the report score 50. Report score 50 is typically displayed on the dashboard 22 below a photo or other practitioner identifier (See FIG. 8). In further aspects, a hospital tab 46 (FIG. 7) opens a hospital field 48 (FIG. 9) for easy entry or selection of various hospitals or clinics. Multiple entries may be added. Additional hospitals increase the points which are also added to a counter 180 to formulate a raw score and in turn to create the report score 50. Multiple additional tabs are provided at data factor tabs column 40 for entry of data factors 170 or data elements and values. Multiple users 30, 32 may access system 100 with data stored in memory associated with the servers. Various searching filters and operations are available for practitioners 30, 32 to search for the purposes of researching and referring their patients and for other purposes as noted herein.

Figure 10:
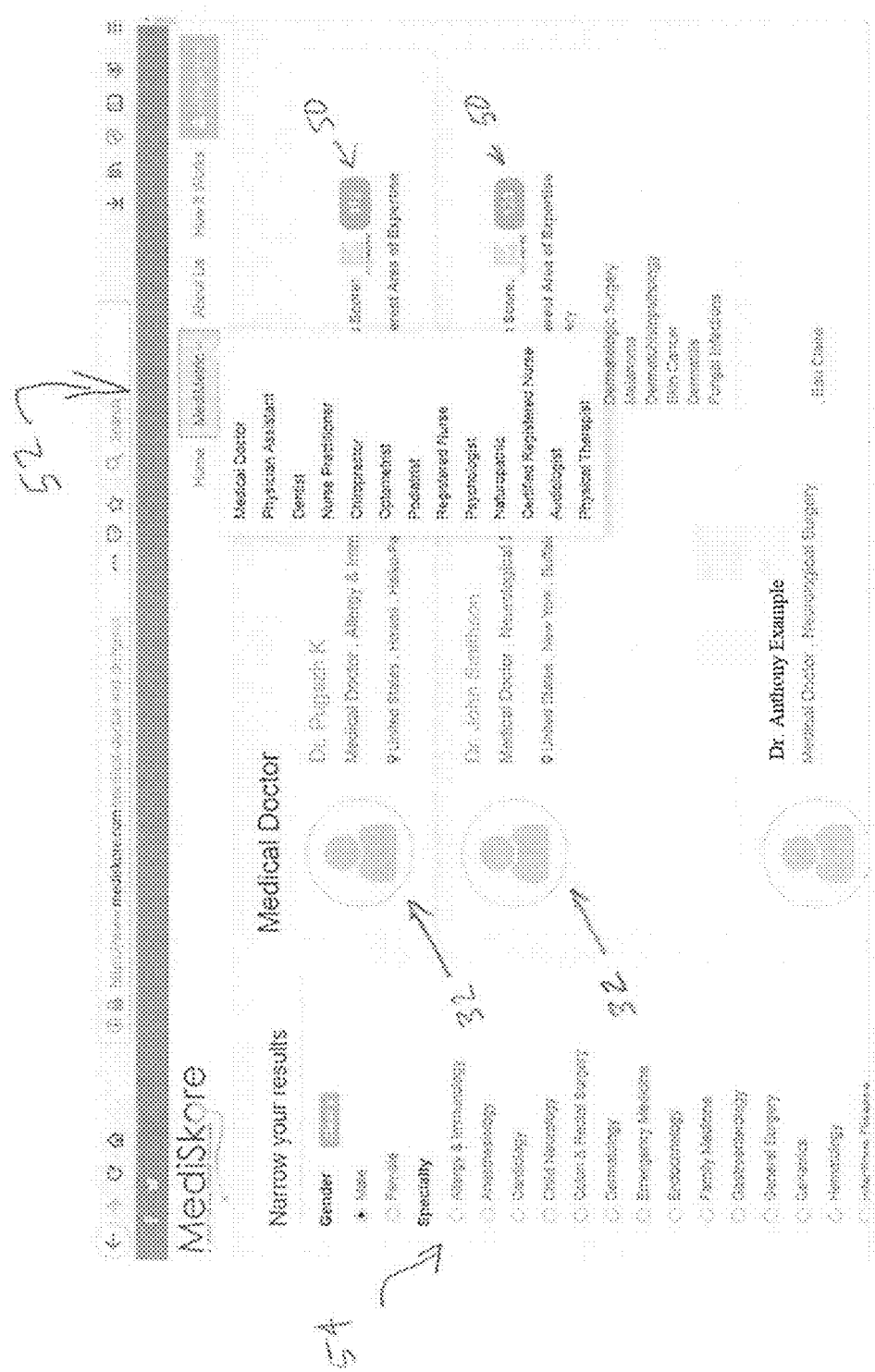
FIG. 10 through FIG. 15 are screen shots in accordance with various aspects of the present invention.

In one aspect with respect to FIG. 10, a search page is presented with a pulldown list for selection of a particular professional to be searched. In one instant the professionals list 52 includes a Medical Doctor tab. Selecting the medical doctor tab returns results of all medical doctors ranked by their report score 50. In further examples additional filters and selection tabs may be used for refined searching and ordering. Specialty filters 54 are included for refined searching. Clicking on a radio button or select tab will return the desired filtered results with practitioners ranked according to report score 50. Numerous specialties and subspecialties are available. In one aspect, such specialties are input by the practitioner at registration. Insertion of a particular specialty is required in order to access or participate in certain features of the system and invention.

Figure 11:
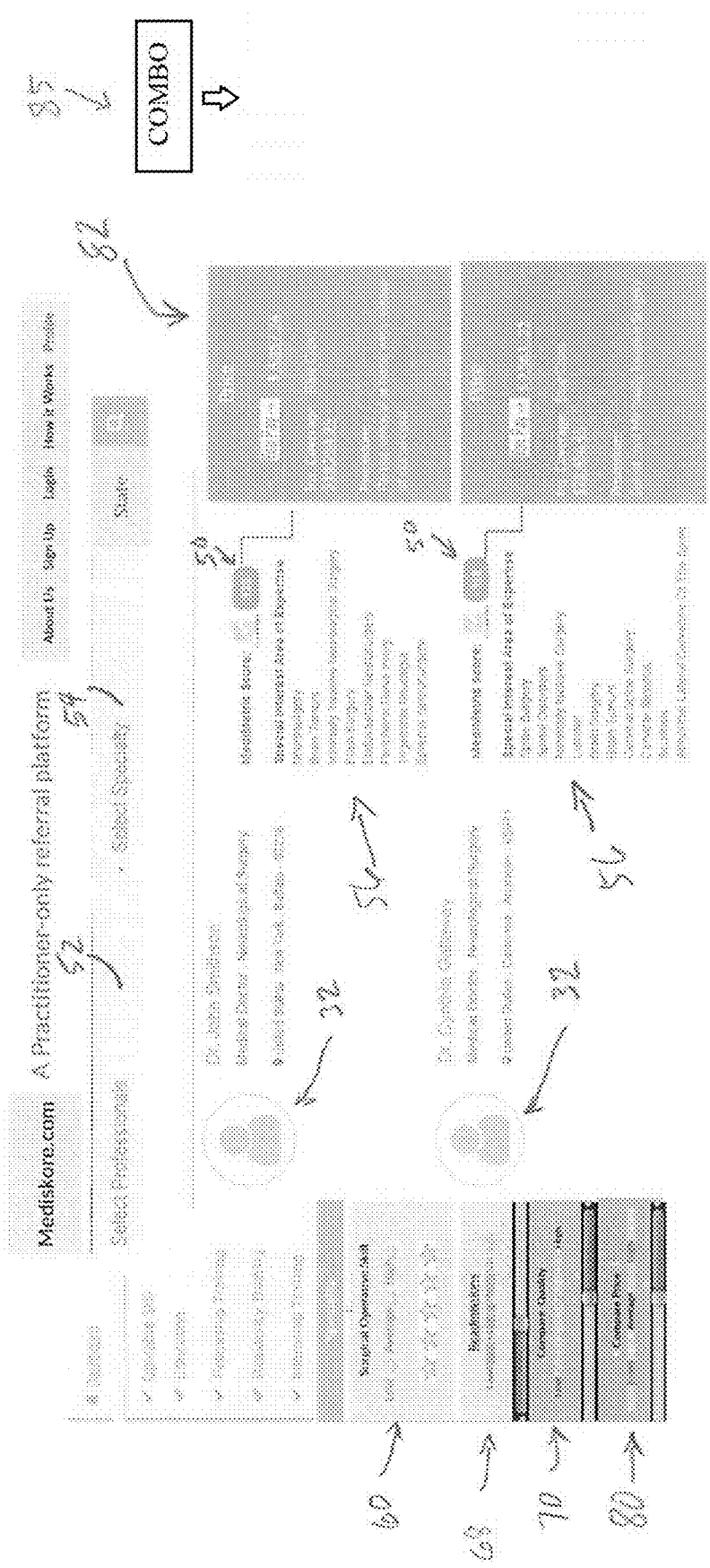

FIG. 11 shows a further page having result of a search, and includes additional filters and reporting information. In addition to specialty filters 54, or gender filter or state filter, in one aspect the system includes a Surgical Operative Skill Filter 60. Surgical Operative Skill filter 60 will filter the search result based on video evaluation data as explained below. An additional filter of Compare Quality 70 and compare price 80 are provided. Compare Quality 70 allows a user to select a range (low, medium, high, for instance) to display results of practitioners 30 based on or ranked according to the selected range. Compare price 80 allow a user to select a price range for comparison, where practitioners are ranked according to the selected price range. A price column 82 may be included in the display, and includes data associated with the respective practitioners 30, 32. The price data in one aspect may include a full spectrum of Medicare information, including volume of procedures, descriptions of procedures, dates, prices and costs for all aspects as is typically provided by and/or reported via Medicare systems. Likewise, pricing and costing data in some aspects is included with respect to private payer insurance or other insurance or payment sources (or utilized together with Medicare data as appropriate), including, for instance, patient volumes, procedures undertaken, conditions treated, and costs, including such information aggregated among multiple providers. In one aspect, such pricing data includes data provided via price transparency systems such as those utilized at www.medifees.com. The same or similar systems in one aspect are used in conjunction with non-Medicare providers.

Figure 12:
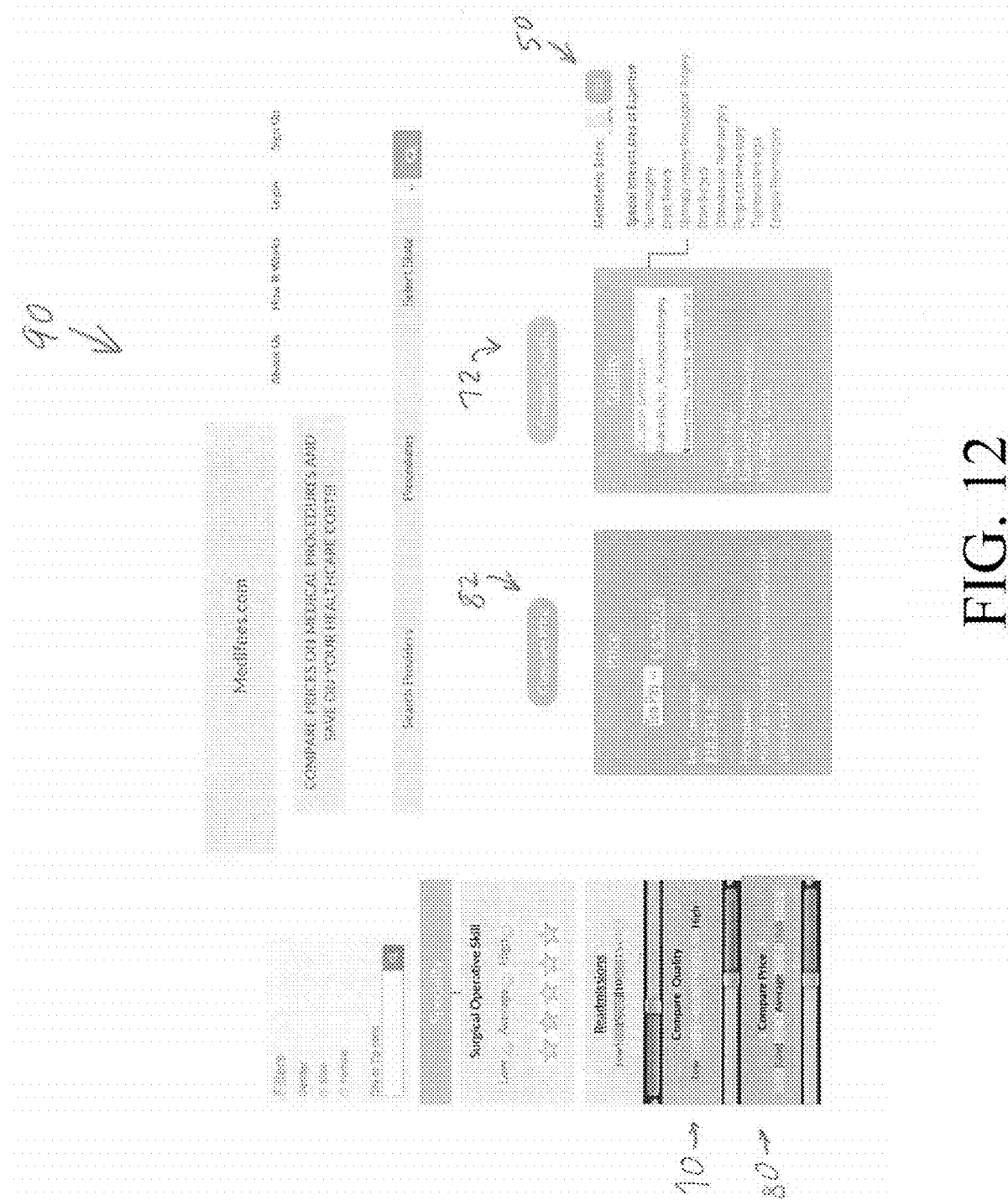

In further aspects and with respect to FIG. 12, a price comparison page 90 is provided and includes additional filters and search tools for presenting quality comparisons. Particularly, the price comparison page 90 is equipped with a filter to select Compare Quality 80 which opens a compare quality field 72 which lists the ranked providers 32 and their respective report scores 50. Multiple providers may be displayed and ranked at page 90. This is in addition to the typical ranking or Compare price column 82 displaying ranked lists of prices for each provider with a listing of the insurance coverage (or Medicare amount) and procedures undertaken along with price data. The price information may include bundled prices showing all provider, hospital, clinic, etc., costs, with a remainder amount ("you pay") which is or was paid by the patient. A practitioner 30, 32 may therefore also assess the costs and provide this information to the practitioner's patients to make better informed referral decisions.

In a further aspect with respect to FIG. 11, a combo column 85 is provided for selecting a weighted combination of both quality and price. For instance, by selecting combo 85, a ranked weighted list of the best quality/price combination is displayed. In one aspect, for instance, certain calculations are included in formulas to blend the pricing points and quality points and providing an combined point value for the ranking. Different weights and factors may be included for obtaining objective measuring criteria so that combination data can be regularly supplied and historical data and trend and big data used for rankings.

In a further aspect with respect to FIG. 11, the sub-specialty or special interest areas of expertise 56 are also presented with each practitioner 30, 32. Such special interests 56 are selected at registration and included in profile data and may also contribute to report score 50. In further aspects, each special interest 56 may be used for searching. For instance, a user may click upon "brain surgery" to re-order or rank practitioners with such further filter. In further aspects, Boolean filters such as AND and/or OR and other Boolean functions may be combined with the filters for refined searching. In further aspect, clicking on compare price 80 tab will rank or include price column 82 information. A slide bar in filter 80 may be used to set the relative value for the filter to display, for instance, the highest costs down to the lowest costs together with the associated report score 50 per practitioner 32.

In further aspects a search Query field or fields are provided for entry of data factors 170. After a registered practitioner logs in with user name and password (received upon confirmed registration as an allowed practitioner with appropriate credentials) the practitioner inputs a desired query. Query results may be displayed on the same page or on a separate pages. Alternatively or in addition to a webpage that includes search query fields, a webpage may include the practitioner input module. This may appear on a single screen or multiple screens to take the practitioner through the recording and scoring steps and process. Multiple pages may be utilized to gather the information and update the counter 180 for scoring. In further aspects a practitioner may Upload the data factor 170 information to system 200.

Figure 13:
Figure 14:
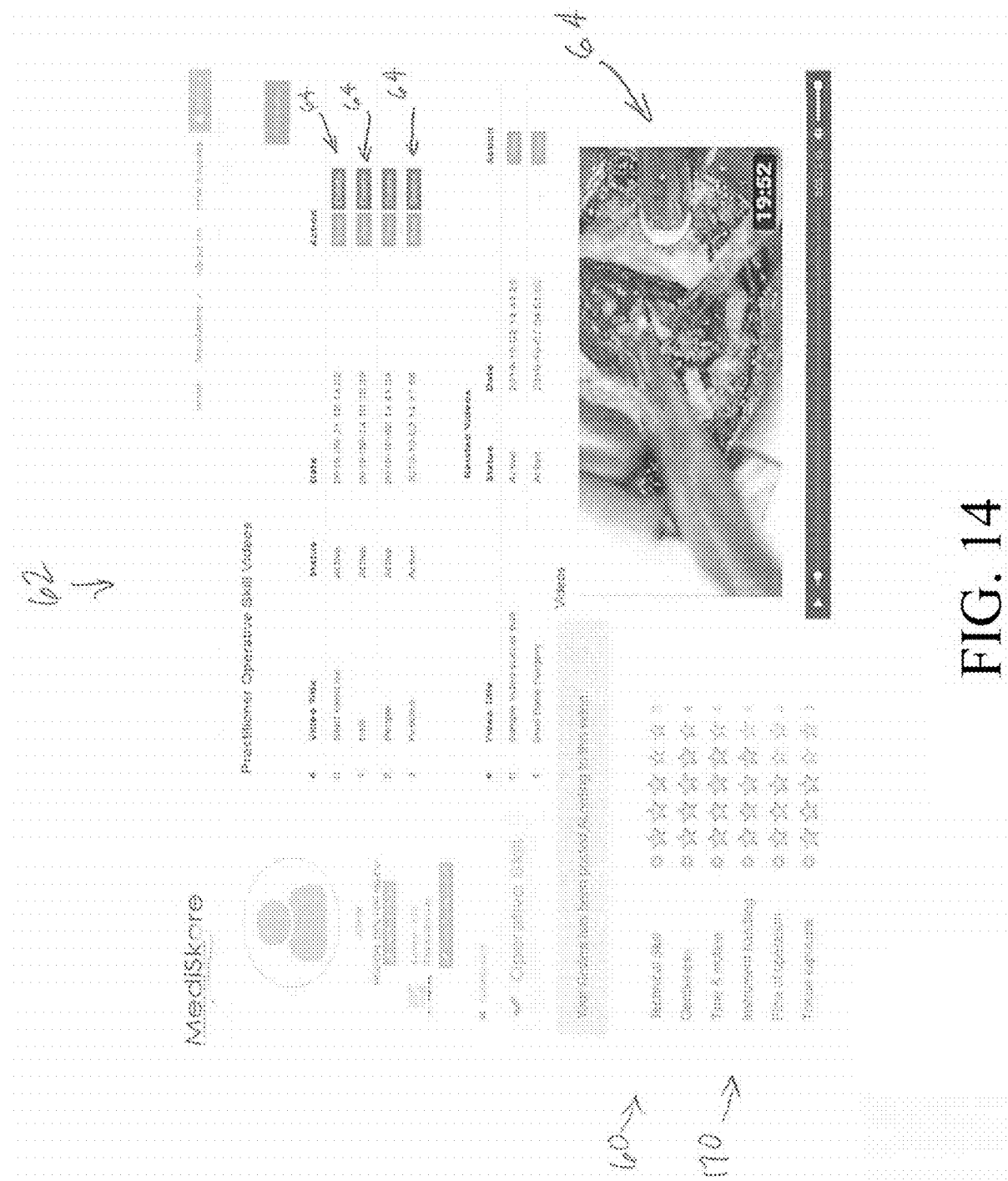

In a further aspect with respect to FIG. 13 and FIG. 14, the surgical operative skill tab 60 (FIG. 7) opens an operative skill field 62 (FIGS. 3, 14) configured to allow a practitioner 30 to upload a video 64 of the practitioner in practice (or showing the procedure being performed by the practitioner). For instance, a practitioner 30 who is a surgeon may upload a video 64 of her performing a surgical procedure (i.e., orthopedic surgeon conducting meniscus removal and clearing). An alert will be provided to peers of the practitioner (i.e., and email message or other alert sent to a pool of orthopedic surgeons having experience with meniscus removal and clearing). Such alert is sent only to the peers of the practitioner based on specialty or sub-specialty areas as determined at registration or at other determination events. The surgeon 32 is thus rated by peers.

With respect to FIG. 13, a practitioner 32 will upload a video 64 by clicking on the Add button 65 and selecting and uploading the desired video of the procedure to be evaluated. When the video is uploaded, in one aspect the practitioner will receive points added to the raw score for recalculating or calculating the report score 50. Multiple videos may be added. Multiple points may be awarded to the practitioner as determined or weighted by the system administrator or software programmer. The practitioner 32 may select to keep the video private, or may select to make the video public by selection at button 66. One the video is made "public", an alert is sent to peers who are invited or allowed to make a peer review or provide video evaluation data. Additional raw points and/or report score 50 points may be provided for making a video public.

In one aspect, a practitioner 32 is rated on a scale of 1 to 5 (with stars, for instance), with 1 indicating the skill expected of a chief resident and 5 indicating the skill of a master surgeon. A subjective fields or data factor 170 for Peer assessment Scores is provided. In one aspect Peer Assessment data factor 170 includes Surgeon Operative Skill. In other aspects Peer Assessment data factor 170 may include assessment of other (non-surgical) skills (i.e., diagnosis, management, follow-up, among other subjective and objective criteria). In one example each video uploaded is added to the surgeon's board certification (specialty) category, only those peer surgeons are able to rate other like-surgeons, and once a surgeon is rated, the score is added to the practitioner's profile and viewable by any practitioner who performs a relevant search query. In alternatives, links to the video are provided to the reviewing practitioners.

In one aspect with respect to FIG. 14, a video 64, such as titled Skull Base Surgery, is displayed at the website for anonymous peer review. The practitioner 30 in this view has list of "related videos" that have been reviewed. Numerous videos may be available for peer review. An incentive or incentives may be provided to a provider 32 to make reviews, including, for instance, an increase in points or report score 50 of their own report score 50, payment of compensation, notoriety, satisfaction in giving back to the community and properly evaluating and educating peers or other practitioners, among other potential incentives. The videos 64 uploaded by the practitioner 30 are provided at the upper portion of field 62 for convenient listing, and may be deleted or viewed or rearranged or minimized as desired.

A scoring scale in one aspect is configured for the Peer Assessment data factor 60, 170 as follows:
Technical Skill: 1-5
Gentleness: 1-5
Time and Motion: 1-5
Instrument handling: 1-5
Flow of operation: 1-5
Tissue exposure: 1-5
Total Points Possible: 30
Lowest Points Possible: 6
Ranking (stars):
25-30 ***** (5 stars)
19-24 ****
13-18 ***
7-12 **
6* (1 star).

At operative skill field 62, a convenient radio button grid is presented so the reviewing practitioner may conveniently evaluate and provide a scoring while watching the adjacent video 64 being played.

The above ranking/scoring may be factored into the Report Score 50 and also displayed as a separate Peer Assessment score. In some aspects mechanisms are in place to assure anonymity of peer reviewers and to factor out bias (such as requiring geographic/competitive separation, blind reviews, multiple peer reviews). In further aspects, the practitioner conducting a peer review is also evaluated based on the quality of the peer review and given a weighted assessment of objectivity which is in turn factored into the review of a practitioner (surgeon in the example) and may or may not impact the reviewing practitioner's report score 50 and/or incentives. In further aspects, videos or still images or other data is uploaded for peer assessments. In addition to receiving a report score 50, a practitioner may also receive an operative skill score which may be separately displayed and or used for filtering (such as filtering via Surgical Operative Skill filter 60 at FIG. 11. In further aspects, a readmissions filter 68 is included for filtering the practitioners. The filter 68 may be selected to display by rank order those practitioners having a low readmissions rate. Again, the filters may be mixed and matched with Boolean operators to assemble sensitive filters, such as practitioners having low readmissions and low price, together with ranked report scores 50, or other criteria as desired.

Figure 15:
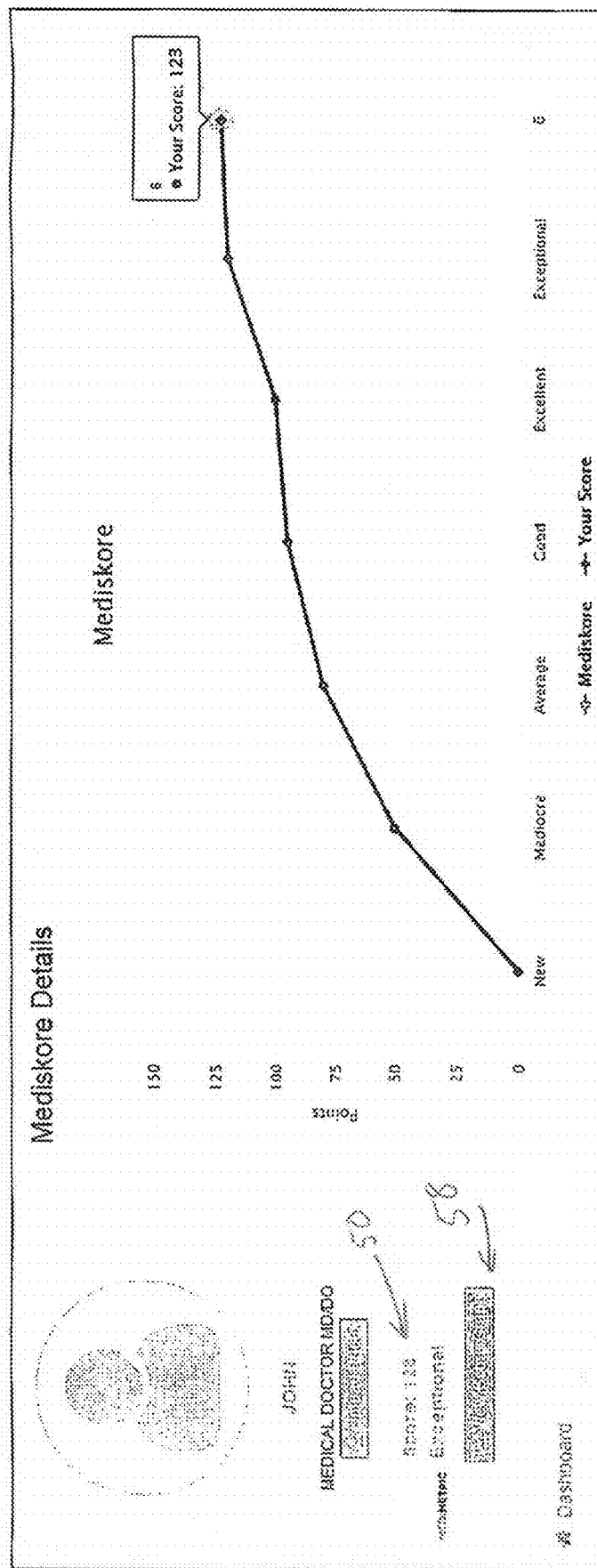

FIG. 15 depicts an example of a screen shot of system 200 and method 100 in operation, and particularly a scoring chart with explanation that further describes the score for each practitioner or practitioner category. A user may click upon the view score graph button 58 at the dashboard to present the graph shown in FIG. 15. A points axis and score or rating axis is charted, and a particular score of an individual practitioner is displayed. From this page a user may click back to the home screen or a dashboard for additional feature views.

Referring again to FIG. 8 is an example of a screen shot in accordance with aspects of the invention, and includes a variety of data entry buttons or fields for including data factors 170. A variety of drop down menus are provided which include preselect data options. For instance, the "Country" drop down menu may be selected, which menu includes numerous available countries for selection. In one instance, if a country other than the United States is selected, a practitioner receives less value or fewer points as compared to a practitioner selecting the United States. The same can be said for the other data factors 170 as desired or configured by the Administrator. A "Degree" drop down menu also includes preselect data from which the practitioner may select. Here again, selecting an MD, for instance, may be configured to provide a greater value or "points" as compared to selecting a different "Degree." Additional drop down fields are provided as may be appreciated, such as City, State, School/College, Graduation Year, etc., and with each or many including drop down menus with preselect data. A list of data factors 170 is also provided so that the practitioner may scroll among the list and select a desired data factor 170 to populate. Clicking on the data factor 170 in one aspects pulls up an entry drop down section 177 into which are positioned additional drop down menus and/or data factor 170 inputs. Check marks signify when a particular data factor 170 has been populated. Once populated, a report Score 160 may be generated as presented herein. The practitioner may then return to a search screen to enter filtering questions or queries to search for referral candidates as needed. Additional features such as chat and notes and a social media components for practitioners are also provided, with short links or tabs for enabling such features.

Further aspects of the invention include computer program products. The computer program products of the invention may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to the invention. It will be understood that each block of the flowchart illustrations and/or block diagrams, and combinations of blocks in the flowchart illustrations and/or block diagrams, can be implemented by computer readable program instructions.

The computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. The computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various aspects of the present invention. In this regard, each block in the flowchart or block diagrams may represent a module, segment, or portion of instructions, which comprises one or more executable instructions for implementing the specified logical function(s). In some alternative aspects, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It should be understood, of course, that the foregoing relates to exemplary embodiments of the invention and that modifications may be made without departing from the spirit and scope of the invention as set forth in the following claims.

What is claimed is:

1. A computer-implemented method of providing practitioner information to registered practitioner-users, the method comprising:
   registering a user as a practitioner-user, the registering requiring at least obtaining a name and NPI number of the practitioner-user;
   receiving, by a server comprising at least one computer processor and memory, a search request from the registered practitioner-user to search for one or more practitioners, the request includes a search query;
   creating a report score for each of the one or more practitioners based on one or more values from a data group comprising: an education score, years of experience score, training score, hospital appointments score, academic appointments score, hospital affiliations score, disciplinary/legal score, licensure score, board certifications score, areas of expertise score, membership affiliations score, insurance accepted score, clinical trials score, operative skill score, outcomes/readmissions score, pricing score, patents score, presentations score, publications score, research score, awards score, professional development education score, athletic teams score, social media score, media and press score, community involvement score, volunteer programs score, type of practice score, foreign language score;
   creating a search results list using the report score for each of the one or more practitioners who match the search query; and
   providing access to the search results list to the registered practitioner-user over a computer network.

2. The method of claim 1 where the one or more values from the data group are based on self-reported information by each of the one or more practitioners.

3. The method of claim 2 where the user becomes a registered practitioner-user only after self-reporting his or her self-reported information regarding the data group.

4. The method of claim 1 where the step of creating a report score for each of the one or more practitioners includes creating a report score for at least one practitioner based at least in part on a skills score based on review of a video of a procedure performed by the at least one practitioner.

5. The method of claim 4 where the at least one practitioner has a first registered specialty, the skills score based at least in part on video evaluation data from a different practitioner, the different practitioner having a second registered specialty, the first registered specialty being the same as the second registered specialty.

6. The method of claim 5 where the at least one practitioner has a first subspecialty, the skills score based at least in part on video evaluation data from a different practitioner, the different practitioner having a second subspecialty, the first subspecialty being the same as the second subspecialty.

7. The method of claim 5 where the different practitioner provides anonymous video evaluation data based on the different practitioner's evaluation of a technical skill presented in the video of the at least one practitioner.

8. The method of claim 1 where the step of creating a search results list includes using pricing information for each of the one or more practitioners who match the search query.

9. The method of claim 8 where the step of providing access to the search results list includes providing access to a display of report scores and pricing information, the report scores and pricing information being displayed simultaneously.

10. The method of claim 9 where the display includes a compare quality filter which allows the user to select a range of quality of practitioners together with a compare price filter which allows the user to select a range of pricing of practitioners.

11. The method of claim 9 where a weighted combination of both quality and price data is displayed.

12. The method of claim 9 where a sub-specialty field or special interest field of a practitioner is included in the display.

13. The method of claim 9 further including a surgical operative skill filter which displays results based on video evaluation data, the surgical operative skill filter displayed simultaneously with the quality filter and the pricing filter.

14. A computer-implemented method of providing practitioner information to registered practitioner-users, the method comprising:
   registering a user as a practitioner-user, the registering including at least obtaining a name and NPI number of the practitioner-user;
   receiving, by a server comprising at least one computer processor and memory, a search request from the registered practitioner-user to search for one or more practitioners, the request includes a search query;
   creating a report score for each of the one or more practitioners based on one or more values from a data group comprising: an education score, years of experience score, training score, hospital appointments score, academic appointments score, hospital affiliations score, disciplinary/legal score, licensure score, board certifications score, areas of expertise score, membership affiliations score, insurance accepted score, clinical trials score, operative skill score, outcomes/readmissions score, pricing score, patents score, presentations score, publications score, research score, awards score, professional development education score, athletic teams score, social media score, media and press score, community involvement score, volunteer programs score, type of practice score, foreign language score;

creating a search results list using the report score for each of the one or more practitioners who match the search query; and providing access to the search results list to the registered practitioner-user over a computer network, where the registered practitioner-user authorizes a third party to report his or her information for use in creating the one or more values associated with the data group.

15. A computer-implemented method of providing practitioner information to registered practitioner-users having been registered utilizing an NPI number and having self-reported one or more data elements from a data group comprising an education score, years of experience score, training score, hospital appointments score, academic appointments score, hospital affiliations score, disciplinary/legal score, licensure score, board certifications score, areas of expertise score, membership affiliations score, insurance accepted score, clinical trials score, operative skill score, outcomes/readmissions score, pricing score, patents score, presentations score, publications score, research score, awards score, professional development education score, athletic teams score, social media score, media and press score, community involvement score, volunteer programs score, type of practice score, foreign language score, to create a report score for each of the registered practitioner-users, the method comprising:

receiving, by a server comprising at least one computer processor and memory, a search request from at least one of the registered practitioner-users to search for one or more practitioners, the request includes a search query;

creating a search results list using the report score for each of the practitioners who match the search query; and providing access to the search results list to the registered practitioner-user over a computer network.

16. The method of claim 15 where the search request is made to search one or more registered practitioner-users.

17. A system for use by registered practitioner-users for identifying practitioners, the system comprising:

a processing unit; and a memory coupled to the processing unit, the memory encoding computer executable instructions that, when executed by the processing unit, perform a method comprising:

receiving a request from a registered practitioner-user to search for one or more of the practitioners, the request includes a search query, the registered practitioner-user having been registered by using an NPI number associated with the registered practitioner-user;

assigning a report score to each of the practitioners, the report score derived from a raw cumulative score based on one or more values from a group comprising: education score, years of experience score, training score, hospital appointments score, academic appointments score, hospital affiliations score, disciplinary/legal score, licensure score, board certifications score, areas of expertise score, membership affiliations score, insurance accepted score, clinical trials score, patents score, presentations score, publications score, research score, awards score, professional development education score, athletic teams score, social media score, media and press score, community involvement score, volunteer programs score, type of practice score, foreign language score;

ranking the one or more practitioners who match the search query based on the report scores to create a ranked results list; and providing access to the ranked results list over a computer network.

18. The system of claim 17 where the one or more of the practitioners are registered practitioner-users.

19. The system of claim 17 further comprising providing pricing information associated with each of the one or more practitioners who match the search query.

20. The system of claim 17 where the report score of at least one of the practitioners is based at least in part on a skills score based at least in part on video evaluation data of a video of a procedure performed by the at least one practitioner.

21. The system of claim 20 where the video had been uploaded to the system by the at least one practitioner.

22. The system of claim 20 where the at least one of the practitioners has a first registered specialty, the skills score based on review of the video by a different practitioner having a second registered specialty, the first specialty being the same as the second specialty.

\* \* \* \* \*